United States Patent [19]

Hassan et al.

[11] Patent Number: 5,661,221
[45] Date of Patent: Aug. 26, 1997

[54] PROCESS FOR THE PREPARATION OF CROSS-LINKED MALEIC ANHYDRIDE COPOLYMERS

[75] Inventors: Mahmoud Hassan; Nagaraj Dixit, both of Middlesex County; Marcus Bentley, Hudson County; David Benedict Viscio, Middlesex County, all of N.J.

[73] Assignee: Colgate-Palmolive Company, New York, N.Y.

[21] Appl. No.: 768,597

[22] Filed: Dec. 18, 1996

[51] Int. Cl.$^6$ ............................................. C08F 8/14
[52] U.S. Cl. ............................. 525/384; 525/327.7
[58] Field of Search ........................ 525/327.7, 384

[56] References Cited

U.S. PATENT DOCUMENTS 3,917,573  11/1975  Parekh ................................ 525/327.7
5,385,729  1/1995  Prencipe et al. ..................... 525/327.7

*Primary Examiner*—Bernard Lipman
*Attorney, Agent, or Firm*—Henry S. Goldfine

[57] ABSTRACT

A process for preparing a cross-linked alkyl vinyl ether/maleic anhydride copolymer having improved linear viscoelastic properties desired in oral care preparations, wherein the cross-linking of an alkyl vinyl ether/maleic anhydride copolymer with a polyol compound is carried out at a temperature of from about 50° to about 90° C. and the cross-linked product is recovered.

11 Claims, No Drawings

PROCESS FOR THE PREPARATION OF CROSS-LINKED MALEIC ANHYDRIDE COPOLYMERS

BACKGROUND OF THE INVENTION

1. Field of the Invention

This invention relates to a process for the preparation of cross-linked maleic anhydride copolymers and more particularly, to a process for the cross-linking of an alkyl vinyl ether/maleic anhydride copolymer with a polyol compound.

2. The Prior Art

Lower alkyl vinyl ether/maleic anhydride (AVE/MA) copolymers, for example a copolymer of maleic anhydride with a $C_1$–$C_4$ alkyl vinyl ether, such as methyl or ethyl vinyl ether, are known to the art and have been long recognized as water soluble ingredients for use in personal care, agricultural, medical and detergent compositions.

In particular, a methyl vinyl ether/maleic anhydride copolymer, commercially available under the trademark "Gantrez" is disclosed in U.S. Pat. Nos. 5,202,112 and 5,334,375, as a thickener and antibacterial-enhancing agent for noncationic antibacterial agents used in oral care compositions such as toothpastes and mouthwashes. Gantrez is a methyl vinyl ether/maleic anhydride copolymer having an average molecular weight (M.W.) of about 30,000 to about 1,000,000 available from ISP Investments, Inc. Gantrez S-97 pharmaceutical grade (M.W. 70,000) is preferred for use in oral compositions.

It is known to the art, e.g. U.S. Pat. No. 5,385,729, that an AVE/MA copolymer having linear viscoelastic properties useful as a thickener in oral care compositions may be obtained by cross-linking the copolymer. Cross-linking the copolymer is carried out during the polymerization of the AVE and MA monomers by including in the reaction medium a preferably moderate, 3 to 15% by weight, amount of an unsaturated cross-linking agent, typically a $C_4$–$C_{30}$ hydrocarbon containing an ethylenically unsaturated group in a non-conjugated, terminal relationship such as 1,7-octadiene, 1,9-decadiene, divinyl glycol, propylene glycol, butanediol, hexanediol and dodecanediol diacrylate.

U.S. Pat. No. 5,385,729 also discloses that the AVE/MA copolymer can be cross-linked by a post polymerization reaction, wherein polyfunctional cross-linking agents reactive with pendant carboxyl groups along the AVE/MA copolymer chain are used. Illustrative cross-linking agents are polyol compounds containing about 4 to about 30 carbon atoms including linear and cyclic polyols such as butane and octadecane diols, polyethylene glycol, glycerol, sucrose and pentaerythritol. The patentee teaches that in such post-polymerization cross-linking process, the anhydride ring of the AVE/MA copolymer must first be opened by hydrolysis to release free carboxy (COOH) groups needed for reaction with the polyol cross-linking agent before the cross-linking reaction can be accomplished. The patentee further teaches that post-polymerization cross-linking of the AVE/MA copolymer is less preferred than cross-linking with ethylenically unsaturated hydrocarbons, as the polyol cross-linking product tends to more easily be subject to hydrolysis with the resulting loss of the desired linear viscoelastic properties.

SUMMARY OF THE INVENTION

The present invention is directed to a process for preparing a cross-linked alkyl vinyl ether/maleic anhydride copolymer, which provides a product having improved linear viscoelastic properties desired in oral care applications, which comprises concurrently reacting in an aqueous solution, at a temperature of from about 50° to about 90° C., an alkyl vinyl ether/maleic anhydride copolymer and a polyol compound and then recovering the cross-linked product.

The polyol cross-linked product prepared in accordance with the process of the present invention when incorporated in dentifrice compositions unexpectedly improves the physical properties of such dentifrice with respect to reduced stringiness and improved extrudability.

DESCRIPTION OF THE PREFERRED EMBODIMENTS

The cross-linked polymer of the present invention is a gel product of a maleic anhydride copolymer with a $C_1$–$C_4$ alkyl vinyl ether, preferably methyl or ethyl vinyl ether which is cross-linked with a polyol compound such as glycerin or sorbitol.

The alkyl vinyl ether/maleic anhydride copolymer used to prepare the gel product of the present invention contains the alkyl vinyl ether and maleic anhydride monomers at a weight ratio of about 1:4 to about 4:1, and is preferably a methyl vinyl ether/maleic anhydride (MVE/MA) copolymer having a molecular weight (M.W.) of from about 30,000 to about 1,000,000. These copolymers are commercially available under the Gantrez trademark previously discussed.

The AVE/MA copolymers are crosslinked by the process of the present invention, creating a linearly viscoelastic material. The copolymers are lightly cross-linked so that they swell and form gels, having strong three-dimensional networks in aqueous systems.

In accordance with the process of the present invention, the polyol cross-linking is performed subsequent to the formation of the AVE/MA copolymer. The cross-linking reaction is carried out in an aqueous medium in accordance with a reaction mechanism which is believed to be a condensation polymerization. Suitable polyol cross-linking agents include sorbitol, xylitol, mannitol, sucrose, fructose, alkyl polyglucoside, glycerin, pentaerythrytol, ethylene glycol and polypropylene glycol, with sorbitol and glycerin being preferred.

Water employed in the preparation of cross-linked copolymer compositions is preferably deionized and free of organic impurities. Water generally comprises from about 60 to 95 percent of the reaction medium in which the cross-linked polymer is prepared. These amounts of water include the free water which is added, plus that which is introduced with other materials, as for example, water entrained in the polyol, such as sorbitol.

The cross-linking reaction is preferably carried out in the presence of a relatively small quantity of a base catalyst. The presence of such a base enhances and accelerates the rate of the cross-linking reaction. Either an organic or inorganic base can be present, at a concentration of about 0.1 to about 2% by weight based on the copolymer and preferably about 0.25 to about 1% by weight. Typical organic bases are, for example, monoethanolamine, diethanolamine, and triethanolamine (TEA). Typical inorganic bases are alkali hydroxides, as for example, sodium hydroxide and potassium hydroxide. Sodium hydroxide is a preferred base catalyst.

In accordance with the preferred embodiment of this invention the process of the present invention is carried out in the presence of a base catalyst, and either glycerin or sorbitol polyol is used as the cross-linking agent, the polyol is present in the aqueous reaction medium at a weight ratio of at least about 40:1 in relationship to the quantity of the AVE/MA copolymer and preferably from about 50:1. In the absence of a base catalyst, the much longer reaction time which is required to effect cross-linking fosters the hydrolysis of the AVE/MA copolymer, and significantly reduces the quantity of anhydride available for reaction with the polyol. In such a case, in the absence of a base catalyst in the reaction medium, the initial weight ratio of polyol to anhydride must be of the order of 5:1 to allow for an adequate, available nonhydrolyzed quantity of anhydride to be present to facilitate sufficient cross-linking to form the desired viscoelastic gel product.

In the preparation of the cross-linked copolymer, the AVE/MA copolymer and polyol cross-linking agent are added to water in a suitable vessel. In the preferred embodiment, i.e., in the presence of an alkali catalyst, a polyol water mixture is first preheated to between about 50° and about 90° C., preferably from about 55° to 75° C. To this polyol/water mixture the AVE/MA copolymer is slowly added under agitation and mixed for about 3 to about 5 minutes. The alkali catalyst is then added to the polyol/water and AVE/MA copolymer mixture. The quantity of catalyst required to accelerate the cross-linking reaction should be such as to maintain the pH of the reaction medium at about 6 to about 8.5. Higher pH levels are to be avoided as the cross-linked product undergoes a phase shift transition from a gel to a sol. The addition of the AVE/MA copolymer to the water/alkali catalyst mixture is performed under constant agitation using a conventional agitation means, such as a mechanical stirrer, or vibrator; the agitation is maintained until the completion of the reaction, generally a period of from about 4 to about 10 minutes after the addition of the AVE/MA is complete.

The cross-linked AVE/MA copolymer prepared in accordance with the subject invention is useful in a variety of personal care products as disclosed in U.S. Pat. No. 5,385,729. The AVE/MA copolymer has been found to be particularly useful in the preparation of dentifrice compositions, such as toothpastes and gels.

In the preparation of a dentifrice composition using a cross-linked AVE/MA copolymer prepared in accordance with the present invention, there is utilized an orally acceptable vehicle, including a water-phase with humectant, which is preferably glycerin or sorbitol or an alkylene glycol such as polyethylene glycol or propylene glycol; wherein, the water is present typically in amount of about 3 to about 50% by weight, more preferably about 5 to about 20%, and the glycerin, sorbitol and/or the alkylene glycol ingredients typically total about 15 to about 70% by weight of the dentifrice, preferably about 25 to about 50%. The polyol cross-linked AVE/MA copolymer can function as a humectant, whereby the need for comparable amounts of other humectants in the dentifrice may be avoided.

Abrasive compounds may be present in the dentifrice and include sodium metaphosphate, potassium metaphosphate, tricalcium phosphate, dihydrated dicalcium phosphate, calcium carbonate, aluminum silicate, hydrated alumina, sodium bicarbonate, and calcined alumina. Preferred abrasives include dicalcium phosphate and siliceous materials, such as silica, and more preferably a precipitated amorphous hydrated silica, such as Zeodent 115, marketed by Huber Corporation. The abrasive is generally present in the dentifrice at a concentration of about 10 to about 60% by weight and preferably about 20 to about 40% by weight.

The polyol cross-linked AVE/MA copolymer is useful as a thickener or gelling agent in the formulation of dentifrices.

The cross-linked AVE/MA copolymer of the present invention is incorporated in a dentifrice composition at a concentration of about 0.1 to about 5.0% by weight and preferably about 0.25 to about 2.0% by weight.

Supplemental thickening agents include natural or synthetic materials, such as, Irish moss, iota-carrageenan, gum tragacanth, starch, polyvinylpyrrolidone, hydroxyethylpropyl-cellulose, hydroxybutyl methyl cellulose, hydroxypropyl methyl cellulose, hydroxyethyl cellulose and sodium carboxymethyl cellulose, and thickening silicas, such as Zeodent 165, marketed by Huber Corporation, and Sylox 15 available from W. R. Grace Corporation. Such supplemental thickening agents present in dentifrice compositions of the subject invention are in proportions of about 0.1 to about 10% by weight, preferably about 0.5 to about 2% by weight.

Surfactants are used in the dentifrice compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

The surfactant is typically present in the dentifrice compositions of the present invention in an amount of about 0.3 to about 5% by weight, preferably about 0.5 to about 2% by weight.

The dentifrice composition of the present invention may also contain a source of fluoride ions or fluorine-providing compound, as an anticaries agent in amount sufficient to supply about 25 ppm to 5,000 ppm of fluoride ions and include inorganic fluoride salts, such as soluble alkali metal, alkaline earth metal salts, for example, sodium fluoride, potassium fluoride, ammonium fluoride, sodium monofluorophosphate, and sodium hexafluorosilicate. Sodium fluoride and sodium monofluorophosphate are preferred.

In addition to fluoride compounds, there may also be included in the dentifrice compositions of the present invention antitartar agents such as pyrophosphate salts including dialkali or tetraalkali metal polyphosphate salts such as $Na_4P_2O_7$, $K_4P_2O_7$, $Na_2K_2P_2O_7$, $Na_2H_2P_2O_7$ and $K_2H_2P_2O_7$, and sodium and potassium tripolyphosphate, long chain polyphosphates such as sodium hexametaphosphate and cyclic phosphates such as sodium trimetaphosphate which are included in the dentifrice composition at a concentration of about 1 to about 5% by weight.

The dentifrice composition of the present invention may also contain a flavoring agent. The flavoring agent is incorporated in the dentifrice composition at a concentration of about 0.1 to about 5% by weight and preferably about 0.5 to about 1.5% by weight.

Flavoring agents which are used in the practice of the present invention include essential oils. Examples of which include oils of spearmint, peppermint, wintergreen, sassafras, clove, sage, eucalyptus, marjoram, cinnamon, lemon, lime, grapefruit, and orange. Of these, the most commonly employed are the oils of peppermint and spearmint. Also useful are such chemicals as menthol, carvone, and anethole.

Various other materials may be incorporated in the dentifrice compositions of this invention, including antibacterial agents such as Triclosan, chlorhexidene, desensitizers such as potassium nitrate, preservatives, silicones, and chlorophyll compounds. These adjuvants, when present, are incorporated in the dentifrice composition in amounts which do not substantially adversely affect the properties and characteristics desired.

The preparation of dentifrices is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices according to the present invention. Further discussion of such oral compositions is presented in Harry's Cosmeticology, Seventh Edition, 1982, edited by J. B. Wilkinson and R. J. Moore, published by Chemical Publishing of New York, pages 609 to 617.

The following examples are further illustrative of the present invention, but it is understood that the invention is not limited thereto. All parts or percentages are by weight and all temperatures are in degrees C, unless specifically stated to be otherwise.

EXAMPLE I

A cross-linked methyl vinyl ether/maleic anhydride (MVE/MA) copolymer was prepared by a post-polymerization process of the subject invention (designated "Process A"); wherein, a water/glycerin solution containing 26 parts by weight glycerin was heated to 65° C. with stirring and to which 5.1 parts by weight of MVE/MA copolymer anhydride (Gantrez S-97) was added as a powder, the weight ratio of polyol to MVE/MA copolymer being 5.1 to 1. Heating, at about 65° C., with stirring was continued for about one hour until a clear gel product was obtained.

For purposes of comparison, the procedure of Process A was repeated using a series of polyol to MVE/MA copolymer ratios of less than 5:1. The viscosity and appearance of the resulting comparative products are recorded in Table I, below, as prepared by Process A and comparative Processes B, C and D. The viscosity in each case was determined from shear-strain versus sheer stress plots, using parallel plates, at 25° C., on a Carri-Med CSL100 Rheometer.

For purposes of further comparison, the procedure of Example I was repeated except a methyl vinyl ether/maleic acid copolymer was used instead of the MVE/MA copolymer, the anhydride ring of the MVE/MA copolymer having been previously opened by hydrolysis. This process is designated Process E. The viscosity and appearance of the product prepared by Process E is also recorded in Table I, below.

TABLE I

| Process | Part MVE/MA | Part Glycerin | Polyol: Copolymer Weight Ratio | Viscosity (cps) | Appearance |
|---------|-------------|---------------|-------------------------------|-----------------|------------|
| A | 5.1 | 26 | 5.1:1 | 18,521 | Gel |
| B | 5.5 | 17 | 3.1:1 | 3,672 | Viscous Liquid |
| C | 5.9 | 9 | 1.5:1 | 470 | Slightly Viscous Liquid |
| D | 6.5 | 0 | Not Applicable | 29 | Thin Liquid |
| E | 5.1 | 26 | 5.1:1 | 117 | Thin Liquid |

Referring to Processes A–D in Table I, it is apparent that a glycerin:MVE/MA, ratio of about 5:1 is required to obtain a cross-linking viscoelastic gel product. It is further apparent from the physical properties of the product obtained by Process E, that if the anhydride ring of the MVE/MA copolymer is opened prior to its reaction with the polyol, that the product is not adequately cross-linked.

EXAMPLE II

The procedure of Example I (Process A) was repeated with a series of different polyol cross-linking agents; wherein, 0.5% or 0.8% NaOH was included in the reaction mixture. In all cases, the product of these processes designated Processes F, G, H, I, and J was a viscoelastic cross-linked gel, similar to the product of Process A. The gels of prepared by Processes F, G, H, I and J formed within a time period of from about 4 minutes to about 10 minutes after the addition of the MVE/MA copolymer, in contrast to the about 1 hour reaction time required in Process A to form a cross-linked viscoelastic gel. The specific weight percent of the ingredients used in Processes F–J to prepare the cross-linked copolymers are recorded in Table II, below.

TABLE II

| Ingredient | Process F | Process G | Process H | Process I | Process J |
|-----------|-----------|-----------|-----------|-----------|-----------|
| MVE/MA | 1.0 | 1.0 | 1.0 | 1.0 | 1.0 |
| Sorbitol (70% Active) | | | | 50.0 | |
| Glycerin | | | | | 50.0 |
| Xylitol | 10.0 | | | | |
| Sucrose | | 20.0 | | | |
| Pentaerythrytol | | | 5.0 | | |
| Water | 88.5 | 78.5 | 93.5 | 48.2 | 48.2 |
| NaOH | 0.5 | 0.5 | 0.5 | 0.8 | 0.8 |
| Total Weight % | 100 | 100 | 100 | 100 | 100 |

EXAMPLE III

Toothpaste compositions having tartar control or antibacterial properties, designated compositions X and Y, respectively, were prepared with a sorbitol cross-linked MVE/MA copolymer gel using the following procedure:

Using the formula quantities presented in Table III, below, the sodium fluoride and the sodium saccharin were dissolved in the water and mixed with a Lightning propeller mixer or equivalent for a period of about 5 minutes to ensure complete dissolution. Separately, a sorbitol cross-linked MVE/MA copolymer gel was prepared in accordance with Process I, of Example II, and was added to prepare a dentifrice by sequentially adding the polyethylene glycol (PEG) humectant; Gantrez; any tetrasodium pyrophosphate (TSPP) tartar control agent; the previously prepared aqueous sodium fluoride/sodium saccharin solution; the dye or titanium oxide colorant; the balance of the NaOH base; and any supplemental humectant and/or rheological control agent, including, glycerin, NaCMC and iota-carrageenan. These ingredients were added to the sorbitol cross-linked MVE/MA copolymer gel in a suitable vessel and mixed with a Lightning or other propeller type mixer for about 20 minutes. After such mixing the mixture was transferred to a Ross planetary type mixer; wherein, the silica abrasive was added and mixed in for about 1 minute at the lowest agitator speed setting of 1, to wet the powder; the Ross mixer vacuum pump was then turned on and the mixture mixed at a speed setting of 5 to 6, under 28 inches of vacuum for about 10 to about 15 minutes, at which time the sodium lauryl sulfate, any Triclosan antibacterial agent and the flavoring ingredients were added and the mixing was continued under full vacuum for an additional period of about 15 minutes.

For purposes of contrast, the procedure of Example III was repeated to prepare tartar control and antibacterial toothpastes designated compositions X-1 and Y-1, respectively, in which no sorbitol cross-linked MVE/MA copolymer was used. In place of the sorbitol cross-linked MVE/MA copolymer, conventional thickening agents, namely iota-carrageenan, thickening silica and additional Gantrez were substituted for the sorbitol cross-linked MVE/MA copolymer.

It was observed that the appearance of dentifrices X and Y, formulated in accordance with the practice of the present invention, were whiter and shinier than those of comparative dentifrices X-1 and Y-1. Further, upon application from a tube of each of the toothpastes to a toothbrush, toothpastes X and Y were found to be easier to extrude and less "stringy" than toothpastes X-1 and Y-1, i.e., the segment extruded onto the brush did not leave a tail extending back to the tube as occurred with the toothpastes X-1 and Y-1.

We claim:

1. A process for the preparation of a cross-linked copolymer gel of maleic anhydride and an alkyl vinyl ether comprising:

(a) preparing in an aqueous solution, a mixture of alkyl vinyl ether/maleic anhydride copolymer and a polyol cross-linking agent;

(b) reacting the mixture at a temperature of from about 50° C. to about 90° C.; and then (c) recovering the gel product from the reaction mixture.

2. The process of claim 1, wherein the polyol cross-linking agent is glycerin or sorbitol and the ratio of glycerin or sorbitol polyol cross-linking agent to copolymer available for cross-linking is in a weight ratio of at least about 40:1.

3. The process of claim 1, wherein an alkali compound is included in the reaction mixture.

4. The process of claim 1, wherein the alkyl vinyl ether/maleic anhydride copolymer is prepared using a $C_1$–$C_4$ alkyl vinyl ether.

5. The process of claim 4, wherein the $C_1$–$C_4$ alkyl vinyl ether is methyl vinyl ether.

6. The process of claim 4, wherein the $C_1$–$C_4$ alkyl vinyl ether is ethyl vinyl ether.

7. The process of claim 1, wherein the polyol cross-linking agent is selected from glycerin, sorbitol, xylitol, sucrose, and pentaerythrytol.

8. The process of claim 3, wherein the alkali compound is sodium hydroxide.

9. The process of claim 3, wherein the alkali compound is present in the aqueous solution at a concentration of about 0.25 to about 2% by weight of the aqueous solution.

10. The process of claim 9, wherein the pH of the aqueous solution is from about 6 to about 8.5.

11. The process of claim 1, wherein the reaction temperature of step (b) is from about 55° C. to about 75° C.

TABLE III

| Ingredients | Toothpaste Composition X (Wt. %) | Toothpaste Composition X-1 (Wt. %) | Toothpaste Composition Y (Wt. %) | Toothpaste Composition Y-1 (Wt. %) |
| --- | --- | --- | --- | --- |
| MVE/MA Copolymer | 0.5 | — | 0.5 | — |
| Water | 14.31 | 8.0 | 18.217 | 15.607 |
| Sorbitol | 29.157 | 30.367 | 23.663 | 20.85 |
| Glycerin | 10.0 | 10.0 | 20.0 | 20.0 |
| PEG | 3.0 | 3.0 | | |
| Gantrez (13% Sol'n) | 7.69 | 11.54 | 7.69 | 15.0 |
| NaOH Base Sol'n | 0.75 | 1.0 | 0.9 | 1.2 |
| TSPP | 2.0 | 2.0 | — | — |
| $TiO_2$ | 0.3 | 0.3 | 0.5 | 0.5 |
| NaF | 0.243 | 0.243 | 0.243 | 0.243 |
| Sodium Saccharin | 0.4 | 0.4 | 0.3 | 0.3 |
| NaCMC Binder | 1.0 | 1.2 | 1.0 | 1.1 |
| Iota-Carrageenan | — | 0.3 | — | 0.4 |
| Zeodent 115 Silica Abrasive | — | — | 20.0 | 20.0 |
| Zeodent 165 Silica Thickener | 1.5 | 2.5 | 1.5 | 1.5 |
| Sylodent 783 Abrasive | 27.0 | 27.0 | — | — |
| Triclosan Antibacterial | — | — | 0.3 | 0.3 |
| Flavor | 0.95 | 0.95 | 1.0 | 1.0 |
| SLS | 1.2 | 1.2 | 1.5 | 1.5 |
| Total Weight % | 100.0 | 100.0 | 100.0 | 100.0 |

* * * * *